United States Patent [19]

Hirae et al.

[11] Patent Number: 5,314,831

[45] Date of Patent: May 24, 1994

[54] METHOD OF AND APPARATUS FOR EVALUATING CRYSTAL RATE IN SILICON THIN FILM

[75] Inventors: Sadao Hirae; Noriyuki Kondo; Seiichiro Sato, all of Kyoto, Japan

[73] Assignee: Dainippon Screen Mfg. Co., Ltd., Japan

[21] Appl. No.: 965,996

[22] Filed: Oct. 23, 1992

[30] Foreign Application Priority Data

Oct. 24, 1991 [JP] Japan .................. 3-306820

[51] Int. Cl.$^5$ ........................................ H01L 21/66
[52] U.S. Cl. ........................................ 437/8; 437/7; 196/626
[58] Field of Search .................. 437/8, 7, 5, 942; 156/601, 626

[56] References Cited

U.S. PATENT DOCUMENTS

| | | | |
|---|---|---|---|
| 5,066,599 | 11/1991 | Kaneta et al. | 437/7 |
| 5,205,900 | 4/1993 | Inoue et al. | 156/601 |
| 5,229,303 | 7/1993 | Donnelly, Jr. et al. | 437/7 |
| 5,232,547 | 8/1993 | Drowley et al. | 437/8 |

OTHER PUBLICATIONS

"Measurement of the Near-Surface Crystallinity of Silicon on Sapphire by UV Reflectance", M. T. Duffy et al., Journal of Crystal Growth 58 (1982), pp. 10–18.
"A Super Thin Film Transistor in Advanced Poly SI Films", Takefumi Oshima et al., Japanese Journal of Applied Physics, vol. 25, No. 4, Apr. 1986, pp. L291–L293.
"Electronic Structure of Silicon", James R. Chelikowsky and Marvin L. Cohen, Physical Review B. vol. 10, No. 12, Dec. 1974, pp. 5095–5107.
"Ion Implantation Damage and Annealing of Silicon as Characterized by Differential Reflectometry", R. E. Hummel et al., J. Electrochem. Soc., vol. 137, No. 11, Nov. 1990, pp. 3583–3588.

*Primary Examiner*—William A. Powell
*Assistant Examiner*—Kevin M. Picardat
*Attorney, Agent, or Firm*—Ostrolenk, Faber, Gerb & Soffen

[57] ABSTRACT

Light in an ultraviolet region is applied to a first sample of single-crystalline silicon substrate and a sample of silicon thin film to be evaluated respectively, to obtain wavelength dependency of a ratio (reflection intensity ratio) $K(\lambda)$ between reflection light intensity values of the samples. A straight line connecting points indicating reflection intensity values at wavelengths 235 nm and 320 nm is obtained to subtract an actual reflection intensity ratio Kr from a virtual reflection intensity ratio Ki provided by the straight line with respect to a wavelength of 270 nm, thereby obtaining an index $\Delta Ks$. In a similar manner, an index $\Delta Ka$ is obtained as to a second sample of silicon which is composed of only true amorphous phases. The degree of non-crystallization of the silicon thin film to be obtained is evaluated by comparing the index $\Delta Ks$ with the index $\Delta Ka$.

11 Claims, 12 Drawing Sheets

METHOD OF AND APPARATUS FOR EVALUATING CRYSTAL RATE IN SILICON THIN FILM

BACKGROUND OF THE INVENTION

1. Field of the Invention

The present invention relates to an evaluation technique in the field of the semiconductor fabrication, and more particularly, it relates to a technique for evaluating a crystal rate or crystallinity in steps of fabricating a silicon thin film.

2. Description of the Background Art

As to a thin film MOS transistor (hereinafter referred to as "TFT") which is obtained by converting an amorphous silicon thin film to a recrystallized film through solid-phase growth the, possibility of apply same to a liquid crystal display, memory or the like has recently been studied because of far superior electric characteristics as compared with a transistor comprising a polysilicon film formed by another method (T. Katoh, IEEE Trans. Electron Devices, Vol. ED-35 (1988), p. 923, for example).

Improved electric characteristics of such a TFT may be obtained by increasing the recrystallized crystal size. It has been recognized that this improvement strongly depends on the amorphous state of the amorphous silicon thin film before solid phase growth. That is, the amorphous silicon of which has characteristics that are varied with deposition conditions, conceivably contains pure amorphous phases and crystal phases in a mixed state. In order to increase the crystal grain size through solid phase growth, in particular, it is necessary to properly control the density of nuclei of crystal phases (hereinafter referred to as "crystal nuclei") contained in the amorphous silicon. If the density of such crystal nuclei is too large, for example, the number of crystal grains is increased since the crystal grains are grown from the nuclei of these crystal phases during the solid phase growth, to reduce the grain size. If the amorphous silicon is completely composed of pure amorphous phases alone with no crystal nuclei, on the other hand, crystal grains are hardly grown therein.

It is possible to control the density of the crystal nuclei by ion-implanting highly concentrated Si atoms etc. into an amorphous silicon thin film or a polysilicon thin film (T. Ohshima, T. Noguchi and H. Hayashi: Jpn. J. Appl. Phys. Vol. 25 (1986), L291).

If the crystal phases can be quantitatively evaluated in advance of solid phase growth, therefore, it is possible to effectively optimize process conditions so that the recrystallized crystal grain size is increased after solid phase growth. When such evaluation is carried out after recrystallization, it is possible to decide whether the recrystallized thin film is defective or not.

To this end, there have generally been proposed various evaluation methods such as Raman spectrometry, X-ray diffraction, Rutherford back scattering and transmission electron beam diffraction.

As to evaluation of amorphous silicon by the Raman spectrometry, Raman band strength of crystals is regarded as the measure for transition from amorphous phases to crystal phases. On the other hand in Raman spectroscopy, a Raman spectrum is separated into crystal phase components and amorphous phase components, to estimate the volume ratio of the crystal phases from integrated intensity values thereof. In "Raman-Scattering Studies of Silicon-Implanted Galluim Arsenide" by M. Holtz and R. Zallen, J. Appl. Phys. Vol. 59 (1986), p. 1946, it is assumed that peak intensity of scattered light obtained by Raman spectrometry correlates with crystallinity in consideration of a single substance, and the scattered peak intensity is reduced as crystallinity is deteriorated. Unfortunately, Raman spectrometry, measuring steps are complicated and a long time is required for measurement, while the measuring apparatus is increased in size.

Evaluation of crystallinity by the X-ray diffraction has problems similar to the above.

Rutherford back scattering is adapted to accelerate light atoms of ionized hydrogen or helium and introduce the same into a sample, to evaluate crystallinity of the sample by analyzing the energy of these ions which are scattered by atomic nuclei and jump out from the sample. As to evaluation of crystallinity, the area of a surface peak of an align spectrum is related to the density of atoms which are displaced from lattice positions, i.e., defective density, to quantify the crystallinity, as in "Back Scattering Spectrometry" by W. K. Chu, J. W. Mayer and M. A. Nicolet, Academic Press, New York, Chap. 2 (1978), In such Rutherford back scattering, however, a long time is required for measurement. On the other hand, transmission electron beam diffraction is adapted to introduce a highly accelerated electron beam into a sample to obtain the crystal grain size from an image of the transmitted electron beam, and hence the sample must be worked into an extremely small thickness, to be capable of transmitting the electron beam. Such working requires a long time, and a longer measuring time is required for transmission election beam diffraction as compared with the Rutherford back scattering. Further, such measurement cannot be carried out during fabrication steps, since this is a destructive test.

In addition, all these prior art methods require complicated and large-sized measuring apparatus, which must be operated by skilled personnel.

SUMMARY OF THE INVENTION

The inventor has confirmed that, when light in the ultraviolet region is applied to a silicon thin film, the intensity of reflected light (hereinafter referred to as "reflection intensity") normalized by a single-crystalline silicon substrate depends on the degree of noncrystallization (crystallinity) thereof, particularly remarkably at a specific wavelength.

When light of the ultraviolet region is applied to a silicon material which is composed of only amorphous phases and a silicon thin film to be evaluated and reflection intensity values thereof are measured through nomalization with reflection intensity of a single-crystal silicon substrate to be obtained as reflection indices thereof, it is possible to evaluate crystallinity, i.e., how the silicon thin film compares in amorphousness to that of silicon material composed of only amorphous phases.

Based on the foregoing, apparatus of the present invention is constructed to evaluate a crystal rate in an objective silicon film including a crystal phase and an amorphous phase.

According to the present invention, at least one single-crystal silicon and a pure amorphous silicon are prepared. Ultraviolet light is applied to the at least one single-crystal silicon to obtain a first reflection intensity Ic of the ultraviolet light reflected by the at least one single-crystal silicon. The ultraviolet light is also applied to the pure amorphous silicon to obtain a second reflection intensity Ia of the ultraviolet light reflected by the pure amorphous silicon. Further, the ultraviolet light is applied to the objective silicon film to obtain a third reflection intensity Is of the ultraviolet light reflected by the objective silicon film.

The first and second reflection intensities Ic and Ia are compared with each other to obtain a first index value $\Delta$Ka. On the other hand, the first and third reflection intensities Ic and Is are compared with each other to obtain a second index value $\Delta$Ks.

Then, the first and second index values $\Delta$Ka and $\Delta$Ks are compared with each other to evaluate the crystal rate in the objective silicon film.

The present invention can be conducted also immediately after deposition of a silicon film, which may be an amorphous silicon thin film or a polysilicon thin film, or immediately after recrystallization of such a thin silicon film by ion implantation, whereby it is possible to predict the recrystallized crystal grain size after a subsequent long-time heat treatment from the result. Thus, it is possible to omit useless steps for optimizing process conditions. Further, it is also possible to quickly evaluate crystallinity after recrystallization.

In addition, the present invention is so simple in structure that evaluation can be executed with relatively small apparatus as compared with a conventional relatively large-sized apparatus of the prior art.

Accordingly, an object of the present invention is to provide a non-contact/non-destructive technique of evaluating crystallinity, which can reduce the measuring time with simple measuring steps, enable measurements to be made with relatively small apparatus, and be carried out readily during fabrication steps.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

A. Evaluation Principle

Before describing an apparatus according to a preferred embodiment of the present invention, the evaluation principle in the present invention is now briefly explained. Assuming that n represents the refractive index of a substance such as a single crystal of silicon and k represents its absorption coefficient, the reflectance R of light which is vertically incident upon the surface of the substance is expressed as follows, with dependency on a wavelength $\lambda$ of the light:

$$R(\lambda) = \frac{(n(\lambda) - 1)^2 + k(\lambda)^2}{(n(\lambda) + 1)^2 + k(\lambda)^2} \quad (1)$$

Figure 3:
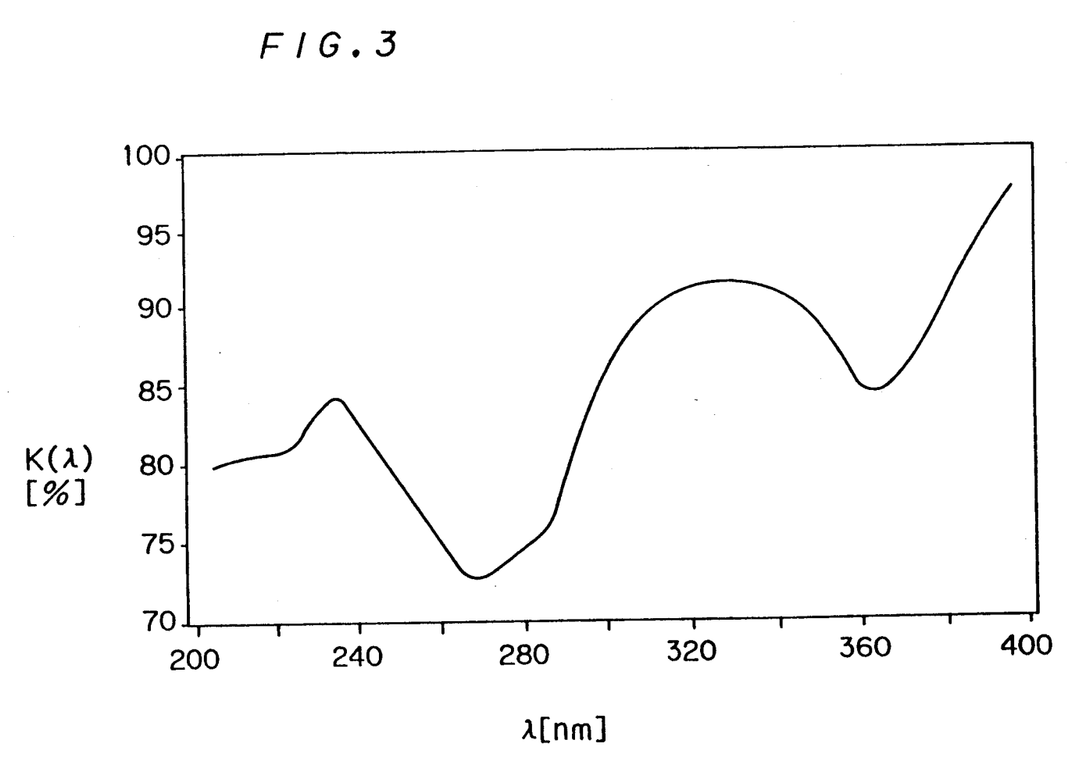
FIG. 3 is a graph showing dependence of reflection intensity upon wavelength.

The refractive index n and the absorption coefficient k, which are varied with substances as a matter of course, are also varied with slight differences of formation conditions in the same substance, particularly in the case of an amorphous silicon thin film or a polysilicon thin film. In the case of silicon, for example, reflectance $Rc(\lambda)$ in a single-crystalline state is different from reflectance $Ra(\lambda)$ in a true amorphous state. The degree of such difference depends on the wavelength $\lambda$, such that a value $Ka(\lambda)$ obtained by dividing the reflectance $Ra(\lambda)$ in a pure amorphous state by the reflectance $Rc(\lambda)$ in a single-crystalline state depends on wavelength as shown in FIG. 3.

The present invention is obtained from the fact that the reflectance depending upon the wavelength represents the degree of non-crystallization or crystallinity, and intensity of reflected light from a sample is measured for obtaining a non-crystallization index of the sample, thereby evaluating crystallinity.

According to the present invention, light in the ultraviolet region (hereinafter referred to as "UV light"), is utilized mainly for the following two reasons: First, if visible light or light having a longer wavelength is employed, the light is easily transmitted through a sample particularly when the sample is formed by a thin film. This leads to a phenomenon such as multiple interference to cause difficulty in evaluation of crystallinity, while it is impossible to measure a correct non-crystallization index due to an influence by reflection from a base substrate of the sample thin film.

Figure 4:
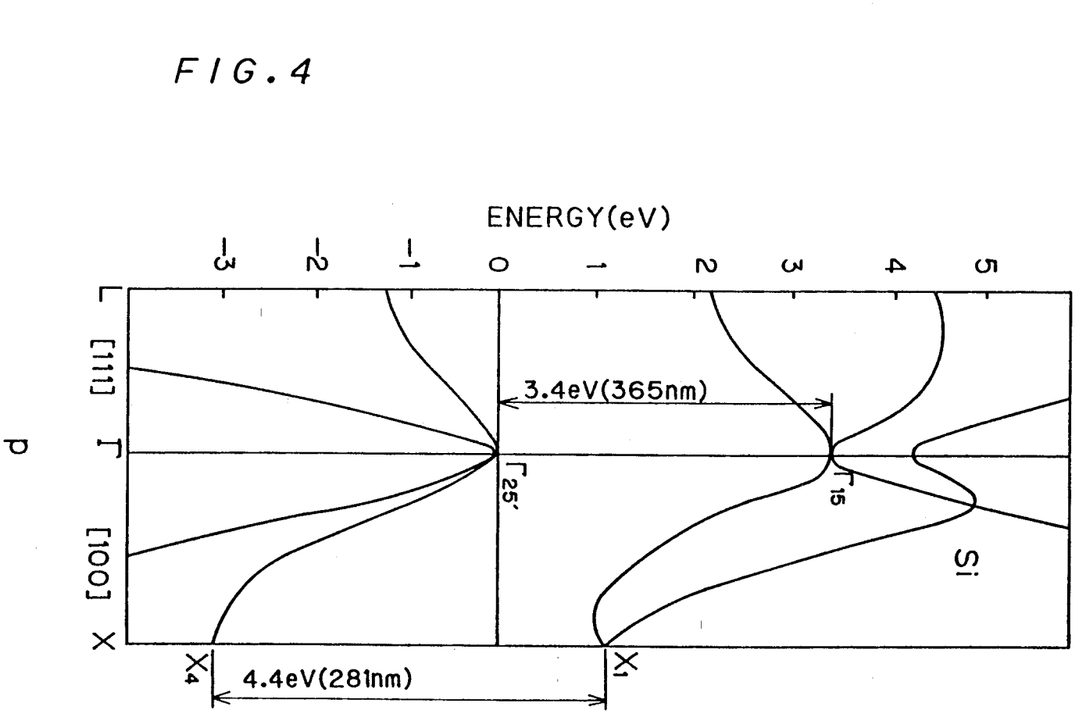
FIG. 4 is a energy band diagram of silicon.

Second, the difference in non-crystallization does not effectively appear in the refractive index n and the absorption coefficient k if visible light is employed, and hence it is impossible to detect slight difference. It is generally known that an absorption band for band-to-band transition exists in the ultraviolet region (200 to 400 nm) in relation to single-crystalline silicon. FIG. 4 shows the energy band of single-crystalline silicon. The axis of ordinates shows the energy which can be taken by electrons, and the axis of abscissas shows wavenumbers p proportionate to the momenta of the electrons (J. R. Chelikowsky and M. L. Cohen, PHYSICAL REVIEW B15 (DECEMBER 1974 P5095). It is understood that the optical constants which have been influenced by the $X_4$-$X_1$ silicon transition exist at about 4.4 eV (281 nm) and $\Gamma_{25'}$-$\Gamma_{15}$ silicon transition exist at about 3.4 eV (365 nm). When no UV light is applied, most of the electrons are filled up in the lower band. When UV light is applied, on the other hand, the electrons are excited by absorption of the energy of the UV light if a state to which the electrons can be exited is in an upper part of the band, to cause transition toward the upper part.

Such a property as to the UV light is specific to a single crystal, and hence the volume ratio of pure amorphous phases to crystal phases contained in an amorphous silicon thin film or a polysilicon thin film exerts an influence on the absorption coefficient of the UV light, as well as to the reflection coefficient. In other words, it is possible to easily mesasure the degree of non-crystallization or crystallinity in high sensitivity even if the sample is formed by a thin film, with no influence by its base substrate.

B. Apparatus Structure

Figure 2:
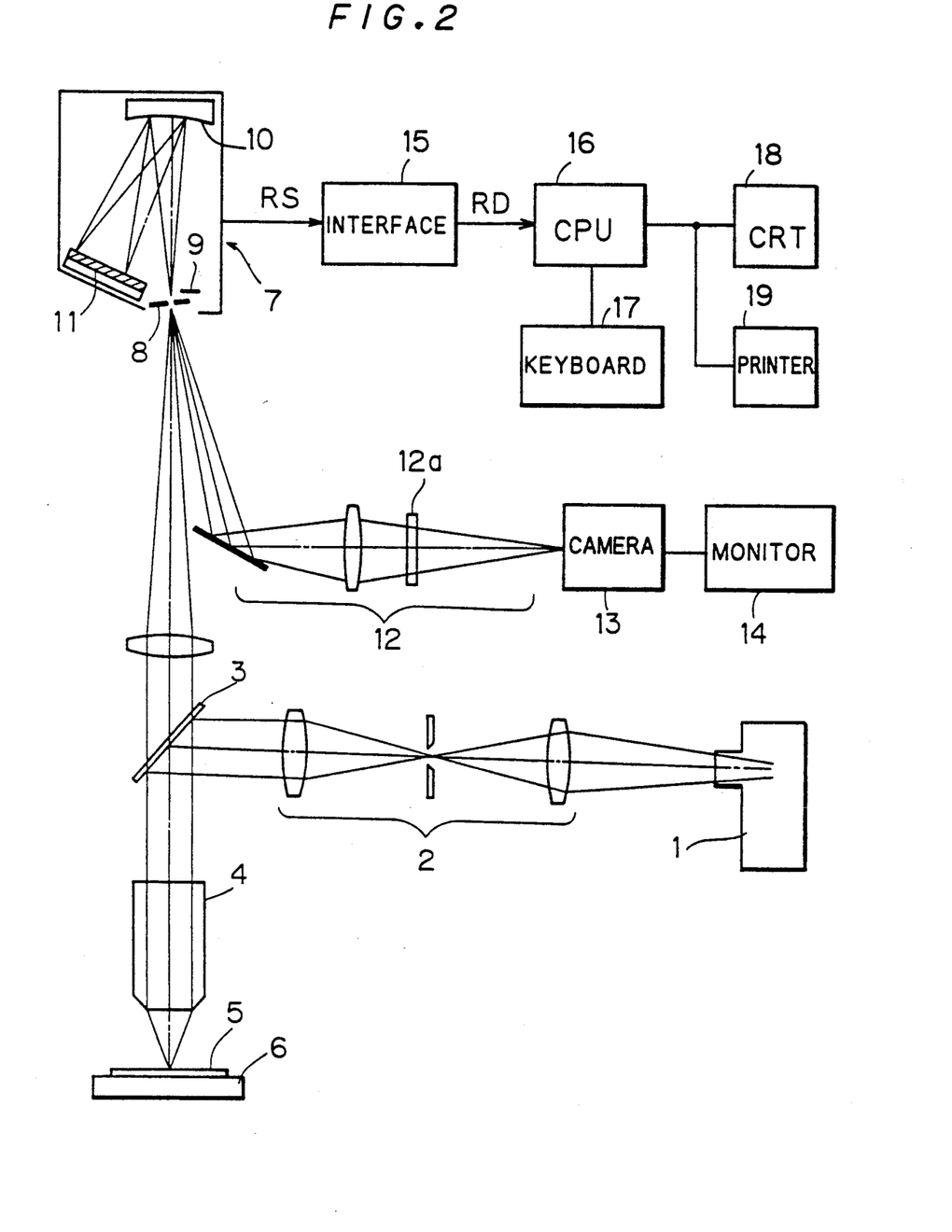
FIG. 2 is a conceptional diagram showing an apparatus according to the preferred embodiment of the present invention.

FIG. 2 schematically illustrates a crystallinity evaluator according to a preferred embodiment of the present invention, which is similar in structure to a film thickness meter employing UV light. UV light outgoing from a deuterium lamp 1 passes through an optical system 2, to be reflected by a half mirror 3. In place of the deuterium lamp 1, the light source may include a Xe lamp, for example, so far as the same emits UV light. The reflected UV light is applied through an objective lens 4 to a sample 5 which is placed on a stage 6, to be reversely reflected. The reflected UV light again passes through the objective lens 4 and is transmitted to a spectrometer 7 through the half mirror 3.

Part of the UV light which is incident upon the spectrometer 7 is reflected by a pinhole mirror 8, to be incident upon a camera 13 through an optical system 12. The optical system 12 is provided with a filter 12a, so that only components of the UV light having wavelengths of a specific range can reach the camera 13, to be monitored by a monitor 14.

On the other hand, the remaining part of the UV light passes through the pinhole mirror 8 and is diffracted by a holographic grating 10 at angles depending upon wavelengths of respective components of the UV light, to be incident upon an image sensor 11, which comprises a line sensor such as CCD, for example. The UV light components of respective wavelengths separated by the holographic grating 10 form images on independent positions, whereby the image sensor 11 can simultaneously receive the UV light components of the respective wavelengths and successively output reflected-light intensity signals RS for the respective wavelengths. A shutter 9, which is adapted to cut off outside light entering the image sensor 11, is closed in dark current measurement of the image sensor 11 or the like, for example.

The reflected-light intensity signals RS for the respective wavelengths are converted to a signal RD through an interface 15, to be transmitted to a CPU 16. The signal RD is processed by the CPU 16 as hereinafter described. Prescribed commands can be inputted through a keyboard 17, and the results of processing can be outputted from a CRT 18 or a printer 19.

C. Method of Measuring Non-Crystallization Index

Description is now made on a method of quantitatively measuring the degree of non-crystallization or crystallinity of an amorphous silicon thin film or a polysilicon thin film and a method of analyzing the signal.

Figure 1:
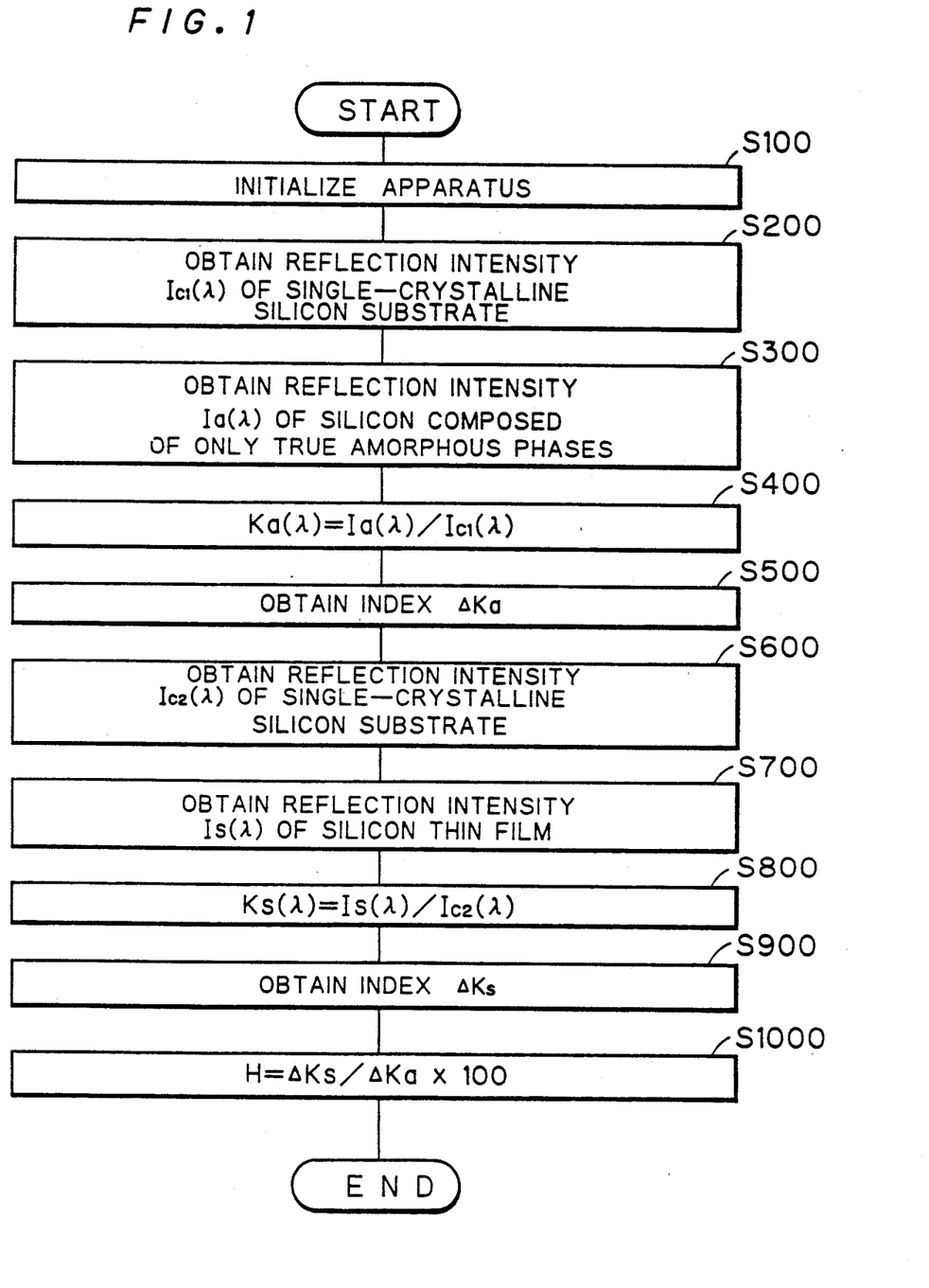
FIG. 1 is a flow chart showing a process according to a preferred embodiment of the present invention.

FIG. 1 is a flow chart of a method of measuring a non-crystallization index according to a preferred embodiment of the present invention.

First, the image sensor 11 is initialized for crystallinity evaluation, which initialization may include dark current correction of the image sensor 11 (step S100). In order to make dark current correction, for example, the shutter 9 shown in FIG. 2 is closed for measurement of the dark current of the image sensor 11.

Then, reflection intensity $Ic1(\lambda)$ of a single-crystalline silicon substrate, which is a first reference sample, is obtained (step S200). In more concrete terms, the single-crystalline silicon substrate is placed on the stage 6 shown in FIG. 2 as the sample 5, so that UV light emitted from the deuterium lamp 1 is reflected upon the sample 5 through the respective optical elements, and the reflected light is diffracted in directions depending on wavelengths $\lambda$ by the holographic grating 10. The image sensor 11 measures reflection intensity values for the respective wavelengths $\lambda$. The aforementioned signals RS and RD, which are adapted to transmit information with respect to the reflection intensity, represent the reflection intensity.

Then, reflection intensity $Ia(\lambda)$ of a second reference sample of silicon, which is composed of only pure amorphous phases, is obtained (step S300). In more concrete terms, a sample of complete amorphous silicon is prepared so that its reflection intensity $Ia(\lambda)$ is obtained in a similar manner to the reflection intensity $Ic1(\lambda)$.

The respective signals representing reflection intensity values $Ic1(\lambda)$ and $Ia(\lambda)$ are transmitted to the CPU 16 and are stored in memories provided in the CPU 16. At a step S400, a reflection intensity ratio is obtained on the basis of these signals, as follows:

$$Ka(\lambda) = \frac{Ia(\lambda)}{Ic1(\lambda)} \tag{2}$$

Since the reflection intensity values of the first and second reference samples are measured by the same UV light, the reflection intensity ratio $Ka(\lambda)$, which is equal to the ratio of reflectance $Ra(\lambda)$ of the sample of silicon composed of only pure amorphous phases to reflectance $Rc(\lambda)$ of the single-crystalline silicon substrate, is also expressed as follows:

$$Ka(\lambda) = \frac{Ra(\lambda)}{Rc1(\lambda)} \tag{3}$$

Thus, it is possible to obtain a signal representative of the reflection intensity ratio shown in FIG. 3 through measurement at the steps S200 to S400.

In each of the steps S200 and S300, the reflection intensity values $Ic1(\lambda)$ and $Ia(\lambda)$ may be obtained by calculation from wavelength dependency of optical constants of single-crystal silicon and pure amorphous silicon described in an optical handbook or the like which is commercially obtainable. As hereinafter described, reflection intensity of a sample to be evaluated is measured and is normalized by the reflection intensity of the first reference sample of single-crystalline silicon, thereby cancelling disturbance factors. The disturbance factors are also cancelled when a reflection intensity value $Ka(\lambda)$ is obtained from two reflection intensity values obtained by calculation.

Figure 5:
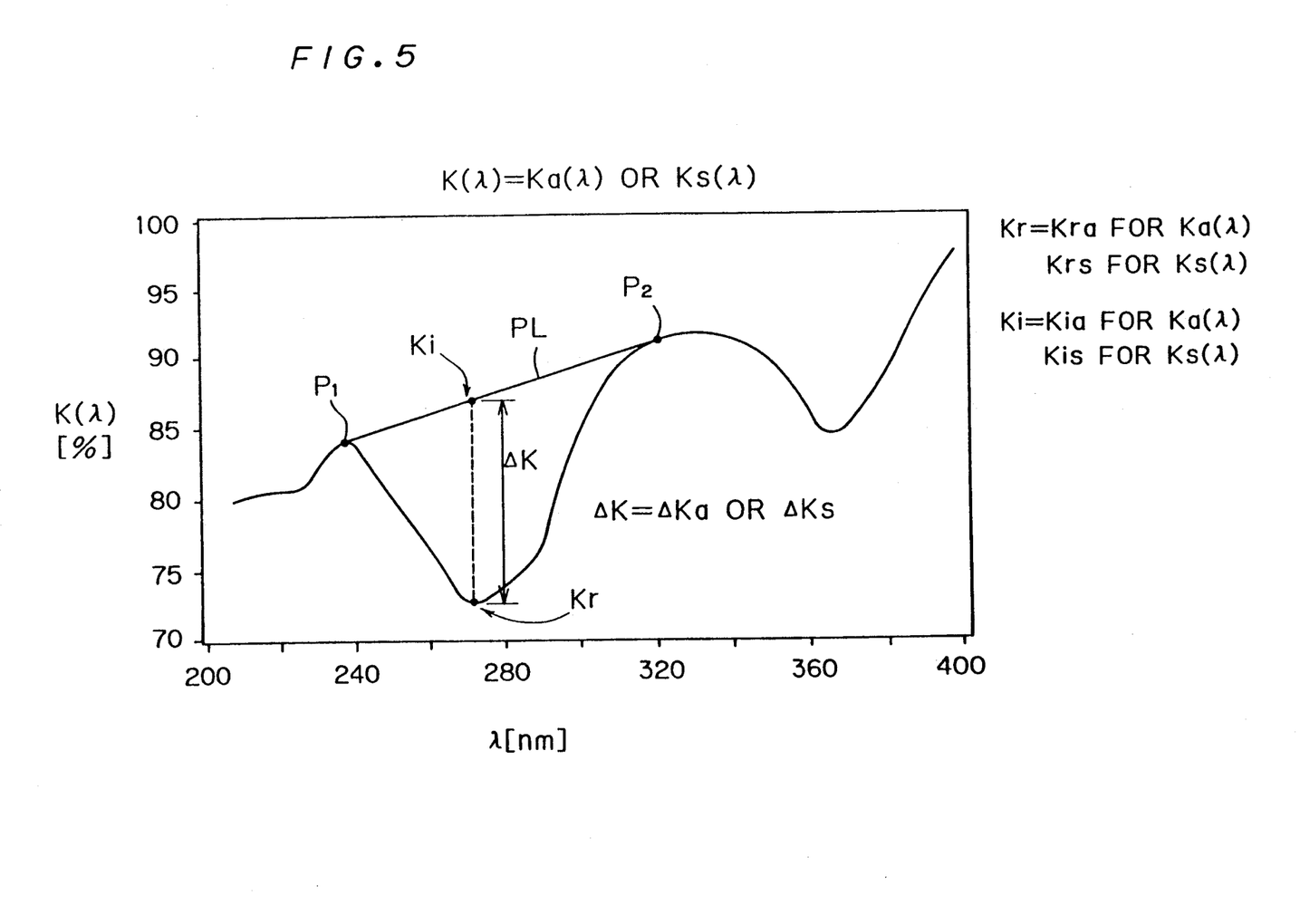
FIG. 5 is a graph showing a process of obtaining an index $\Delta$K.

Then, an index $\Delta Ka$ is obtained at a step S500. This index $\Delta Ka$ corresponds to an index $\Delta K$ where the sample to be compared with the single-crystalline silicon is pure amorphous. This index $\Delta K$ is generally defined as the degree of reduction of a reflection intensity rate $K(\lambda) = I1(\lambda)/Ic(\lambda)$ around $\lambda 0 = 270$ nm, where $I1(\lambda)$ and $Ic1(\lambda)$ are reflection intensities of objective silicon (pure amorphous or sample silicon) and a single-crystal silicon, respectively. Referring to FIG. 5, an actual reflection intensity ratio Kr, which is the local minimum in the curve at $\lambda 0 = 270$ nm, is subtracted from a virtual reflection intensity ratio Ki provided by a straight line PL which connects points P1 and P2 indicating reflection intensity values at two wavelengths of 235 nm and 320 nm separated from λ0=270 nm by constant wavelengths, to obtain the index ΔK=ΔKa.

In FIG. 5, the values K and Ki for Ka(λ) are indicated as Kra and Kia, while those for Ks(λ), which will be described later, are indicated as Krs and Kis.

Figure 6:
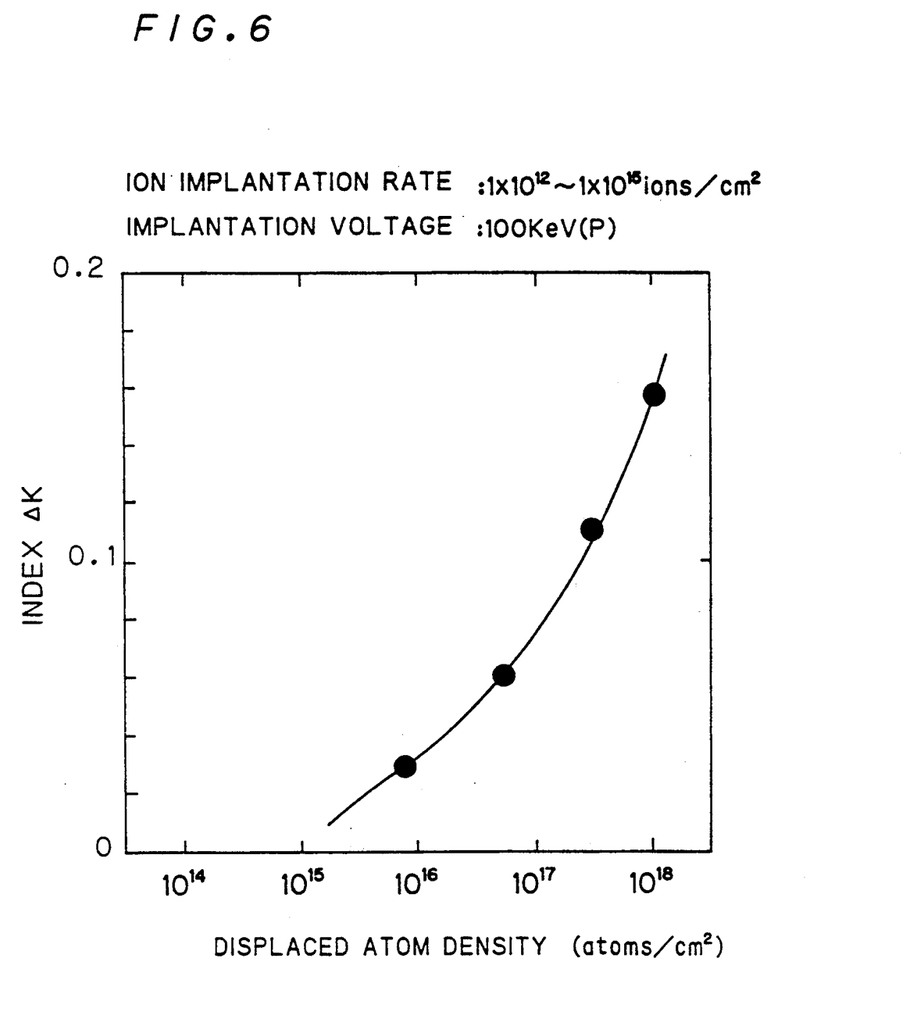
FIG. 6 is a graph showing the index $\Delta$K and displaced atom density.

While the reflectance represents the degree of non-crystallization of silicon as already described, it is possible to quantitatively evaluate the degree of crystallization by employing the index ΔK. In order to confirm the relation between the index ΔK and the degree of non-crystallization in a sample silicon, phosphorus was ion-implanted into a single-crystalline substrate in ranges of an acceleration voltage of 100 KeV and an implantation rate of $1 \times 10^{12}$ to $1 \times 10^{15}$ ions/cm² to destroy the crystal lattice and make an amorphous state, so that density of silicon atoms displaced from regular lattice positions was quantified by Rutherford back scattering. Referring to FIG. 6, plotted is relation between the result and the degree of reduction (index ΔK) of reflection intensity at a wavelength of 270 nm in a reflection spectrum obtained by applying UV light to the sample. Since these values strongly correlate with each other, it is understood that the index ΔK reflects the degree of non-crystallization. The crystal grain size after recrystallization can be predicted by recognizing the degree of non-crystallization, as hereinafter described.

Then, a sample to be evaluated, which may be a silicon thin film such as an amorphous silicon thin film or a polysilicon thin film formed on a glass substrate, for example, is employed to obtain the index ΔKs (steps S600 to S900). The amorphous silicon may be mixture of a pure amorphous phase and a single-crystal phase.

At the step S600, reflection intensity Ic2(λ) of a single-crystal silicon substrate is obtained. The single-crystal silicon substrate may be identical to that used for obtaining Ic1(λ), or alternatively, may be another substrate of the same kind of that used for obtaining Ic1(λ). This step is adapted to measure the reflection intensity of the single-crystal silicon in the same measuring environment as the sample to be evaluated, in order to cancel disturbances during measurement. The reflection intensity Ic2(λ) is obtained in a similar manner to the reflection intensity Ic1(λ).

Then, reflection intensity Is(λ) of the silicon thin film serving as the sample to be evaluated is obtained at the step S700, also in a similar manner to the reflection intensity Ic1(λ). Signals representative of the reflection intensity values Ic2(λ) and Is(λ) are transmitted to the CPU 16 and stored in the memory. Then, a reflection intensity ratio is obtained at the step S800 as follows:

$$Ks(\lambda) = \frac{Is(\lambda)}{Ic2(\lambda)} \quad (4)$$

Then, the index ΔKs is obtained at the step S900 similarly to the step S500. Since the volume ratio of true amorphous phases contained in the sample of the silicon thin film to the overall thin film is not greater than that of silicon composed of only true amorphous phases, there is the following relation:

$$\Delta Ks \leq \Delta Ka \quad (5).$$

Thus, it is possible to quantitatively express the degree of on-crystallization of the silicon thin film with an upper limit of 100 by using the following non-crystallization index H (step S1000):

$$H = \frac{\Delta Ks}{\Delta Ka} \times 100 \quad (6)$$

Figure 7:
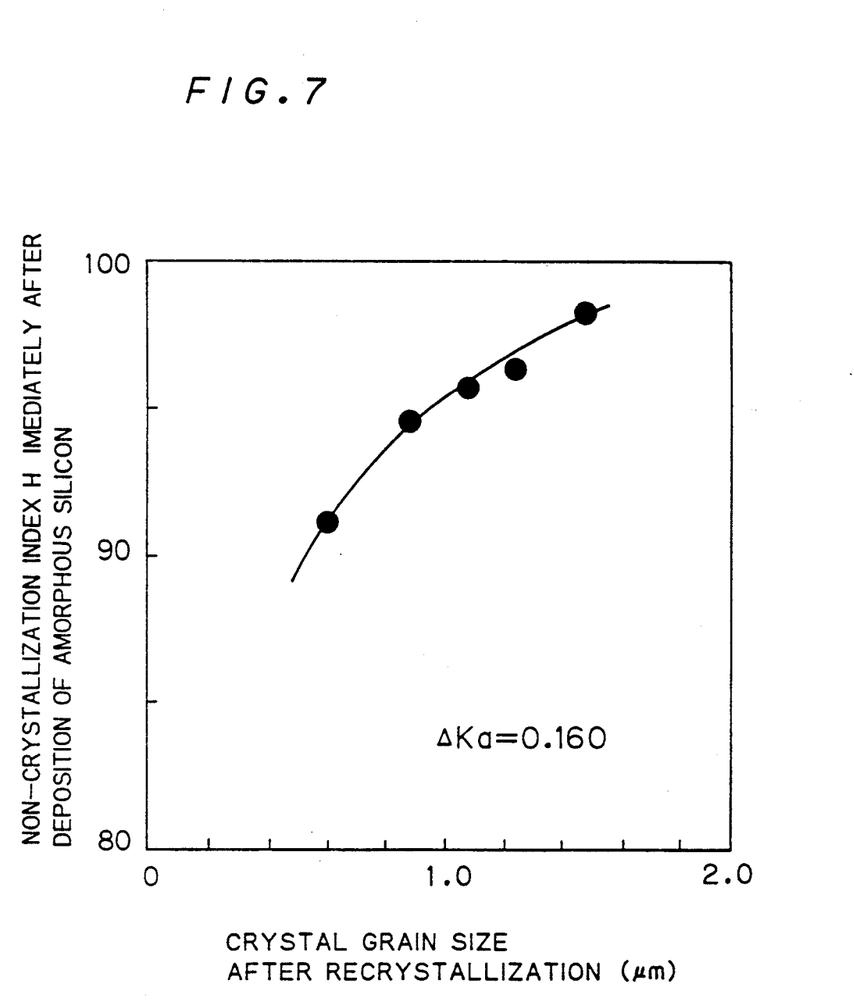
FIG. 7 is a graph showing correlation between a crystal grain and a non-crystallization index.

Referring to FIG. 7, plotted is relation between the non-crystallization index H measured immediately after deposition of amorphous silicon thin films and the crystal grain size measured after a subsequent long-time heat treatment for tens of hours. The amorphous silicon thin films were deposited on respective glass substrates by decompressed vapor deposistion under a common temperature of 550° C., where respective films are formed under different pressure. The as-deposited thin films were heat treated at a temperature of 600° C., while it was assumed that ΔKa=0.160. From the result, it is understood possible to predict the fact that the recrystallized crystal grain size after a long-time heat treatment is increased in proportion to the non-crystallization index obtained before the heat treatment step.

Figure 8:
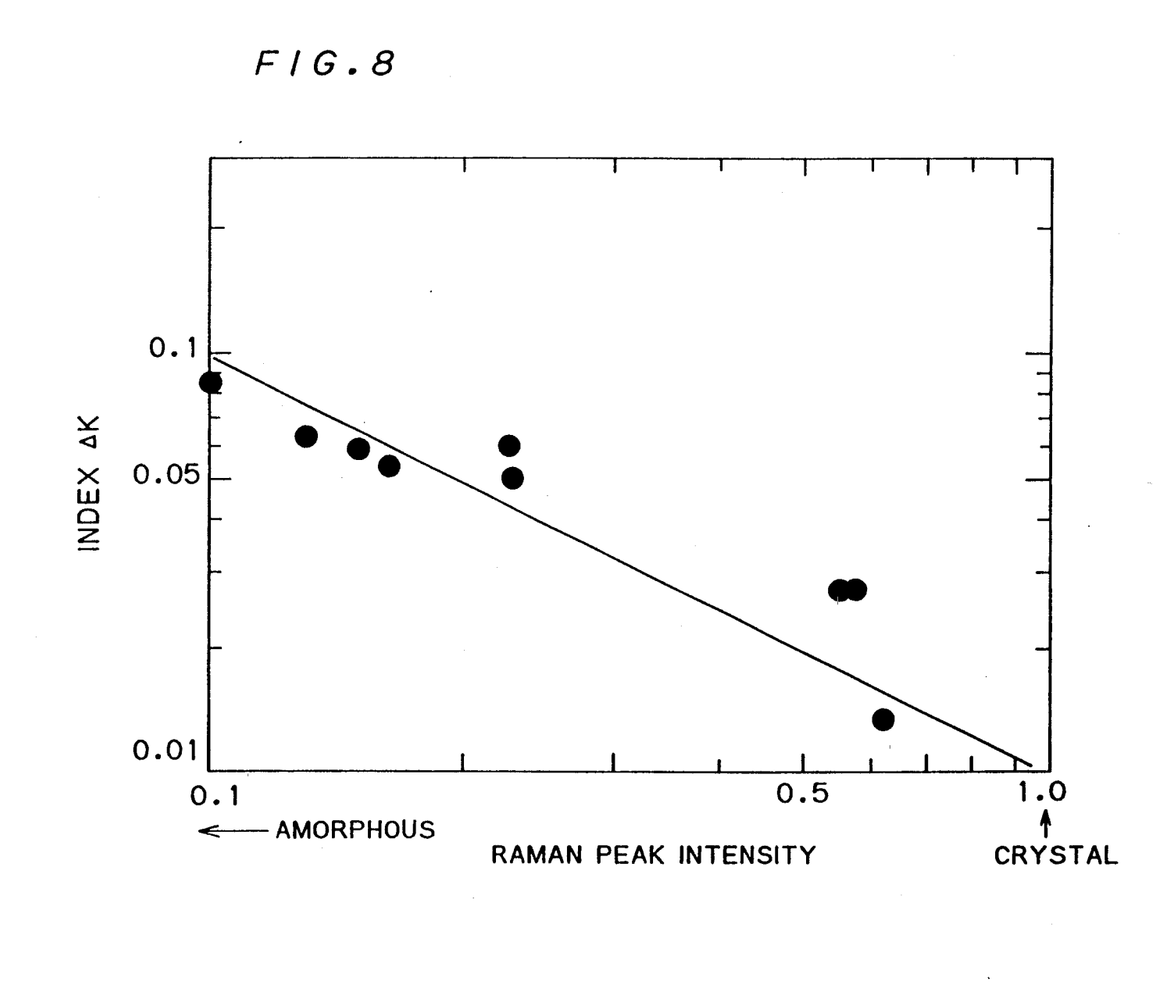
FIG. 8 is a graph showing correlation between the index $\Delta$K and reman peaks.

Referring to FIG. 8, plotted on a long-log scale is the relation between peak intensity of Raman spectrums of recrystallized silicon thin films obtained by heat treating amorphous silicon thin films deposited on respective quartz substrates and the degree of reduction (index ΔK) of reflection intensity at a wavelength of 270 nm in reflection spectrums obtained by applying UV light to the samples after recrystallization. This graph shows a straight line having inclination of −1, whereby it is understood that crystallinity can be evaluated by the index ΔK also after recrystallization.

Figure 9:
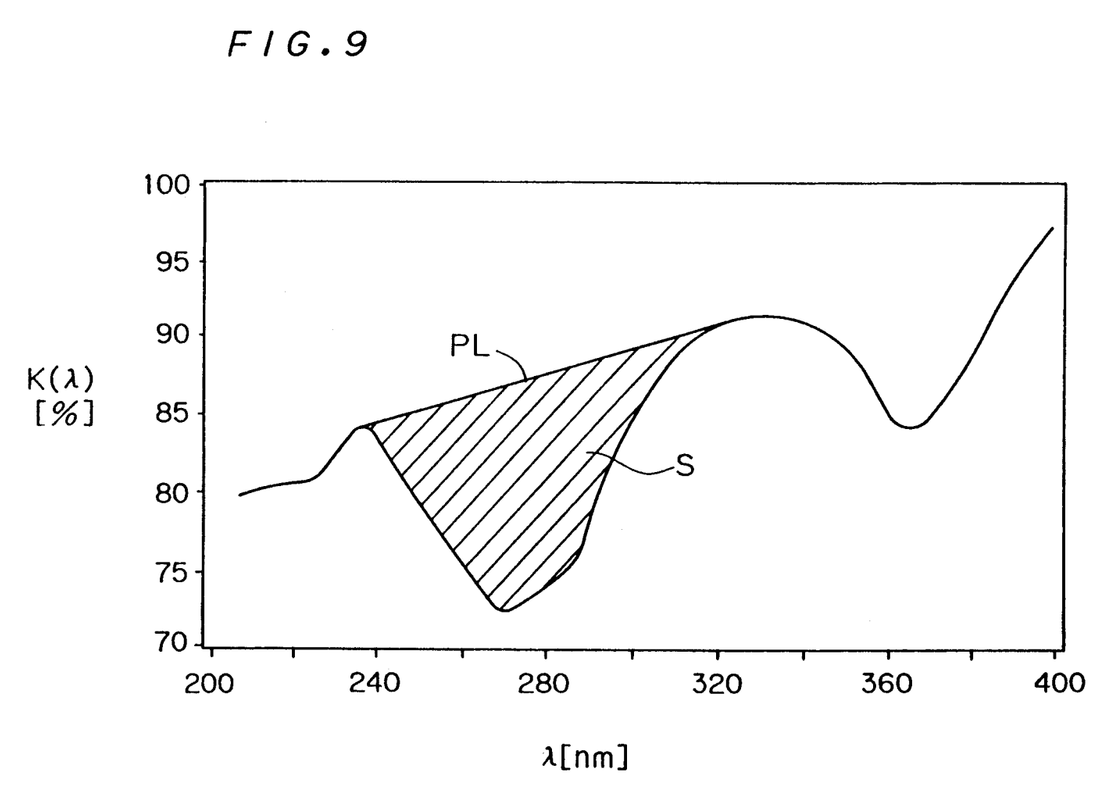
FIGS. 9 and 10 are graphs showing other preferred embodiments of the present invention.

Another index may be employed in place of the index ΔK. The inventor has also confirmed that measurement can be made in higher sensitivity when an area S (FIG. 9) of a portion, shown by slant lines, enclosed by a straight line PL and a graph expressing reflection intensity ratios is employed as an index. This corresponds to steps of measuring indices ΔK for respective wavelengths and obtaining the total sum thereof, which is hardly influenced by external noises.

Figure 10:
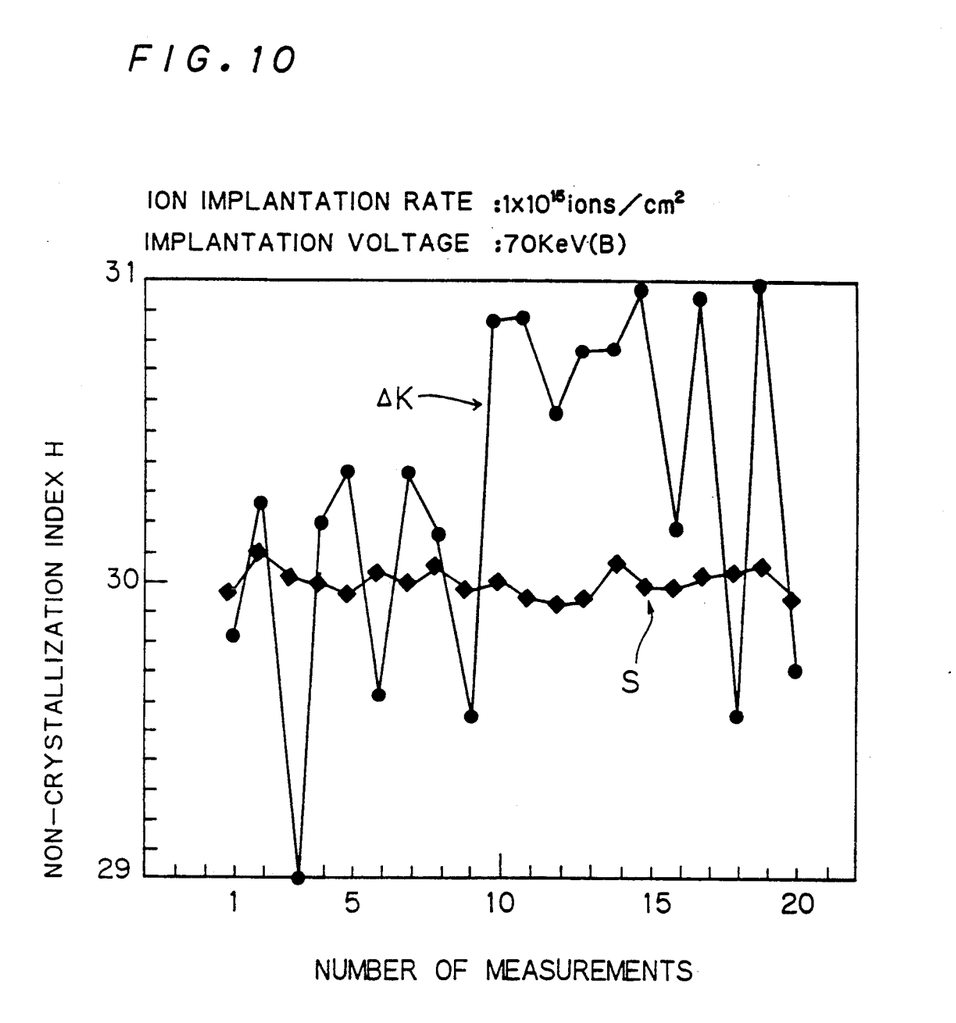

FIG. 10 shows non-crystallization indices obtained by comparing the cases where the area S is employed as an index and the index ΔK is employed to carry out repetitive measurement as to a sample. It is understood from FIG. 10 that a result having superior repeatability is obtained when the area S is employed as the index.

Figure 11:
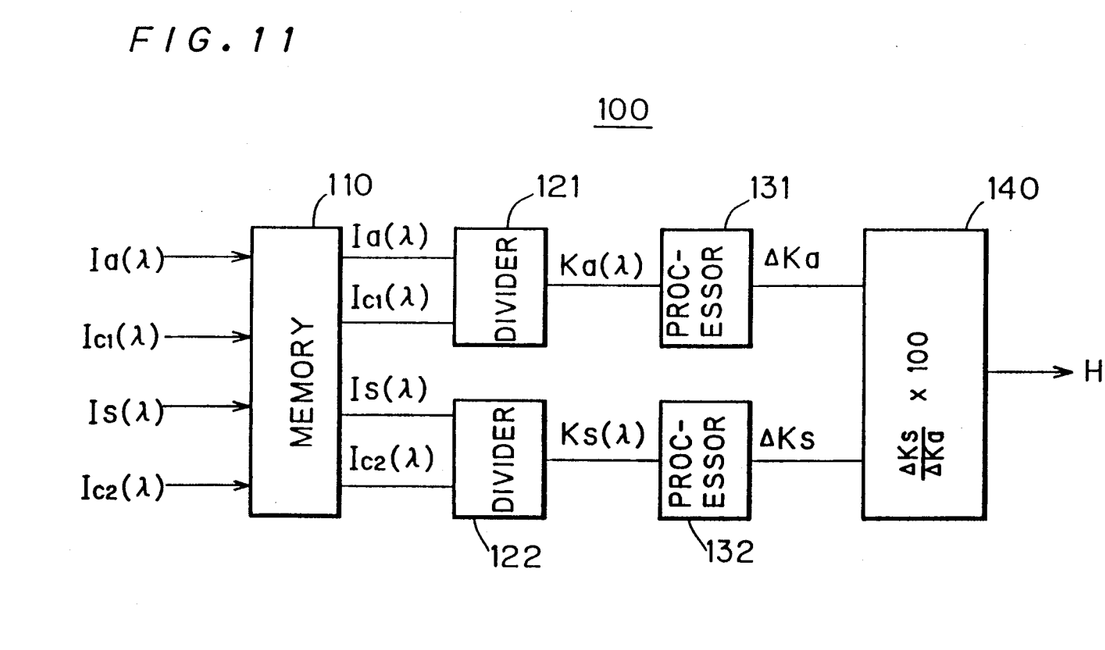
FIGS. 11 and 12 are block diagrams employable in place of the CPU shown in FIG. 2.

FIG. 11 is a block diagram showing a hardware processor 100 employable in place of the CPU 16 in FIG. 2, which processor 100 is adapted to obtain the index H defined by the expression (6). The processor 100 comprises a memory 110 to which the signals representative of the reflection intensities Ia(λ), Ic1(λ), Is(λ) and Ic2(λ) are inputted. The memory 110 stores these signals. The signals Ia(λ) and Ic1(λ) are delivered to a divider 121 and the ratio Ka(λ) is obtained in accordance with the expression (2). On the other hand, the signals Is(λ) and Ic2(λ) are delivered to another divider 122 and the ratio Ks(λ) is obtained in accordance with the expression (4). The signals Ka(λ) and Ks(λ) are transmitted to processors 131 and 132, respectively.

Figure 12:
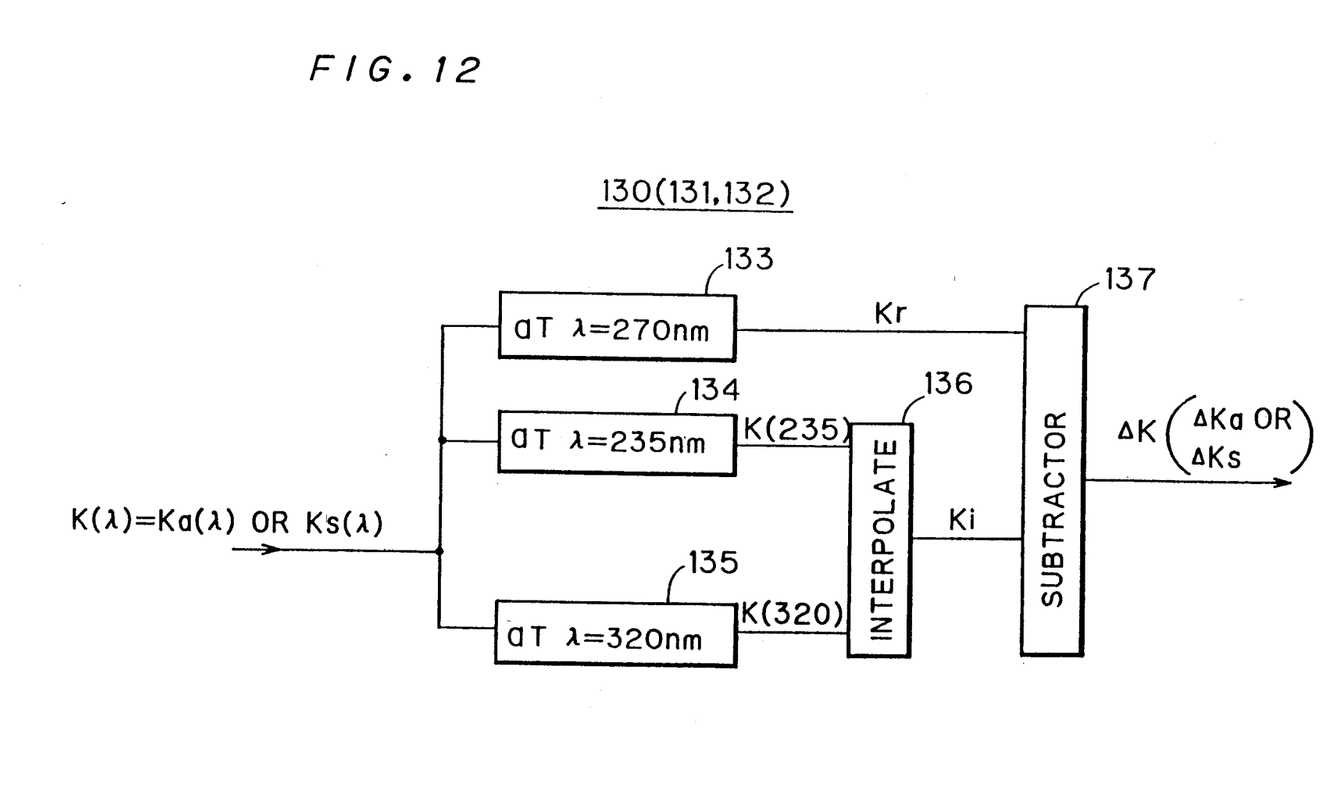

FIG. 12 illustrates a processor 130 employable as the processor 131 or 132. The processor 130 comprises extractors 133–134 operable to extract respective values of the signal K(λ) at λ=270 nm, 235 nm and 320 nm, respectively. Signals K(235) and K(320) representative of the values at λ=235 nm and 320 nm are delivered to an interpolator 136. The interpolator 136 interpolates the signals K(235) and K(320) to λ=270 nm to obtain the value Ki in accordance with FIG. 5. A signal representative of the value Ki is inputted in a subtractor 137 together with a signal representative of a value Kr which is obtained in the extractor 133.

The subtractor 137 subtracts the signal Kr from the signal Ki to obtain an index $\Delta K$ ($=\Delta Ka$ or $\Delta Ks$) in accordance with FIG. 5. Signals representative of the value $\Delta Ka$ and $\Delta Ks$ are transmitted to a divider 140 (FIG. 11) and an index H is calculated in accordance with the expression (6).

While the invention has been shown and described in detail, the foregoing description is in all aspects illustrative and not restrictive. It is therefore understood that numerous modifications and variations can be devised without departing from the scope of the invention.

We claim:

1. A method of evaluating a crystal rate in an objective silicon film including a crystal phase and an amorphous phase, said method comprising the steps of:
   (a) preparing a first sample of at least one single-crystal silicon and a second sample of pure amorphous silicon;
   (b) applying ultraviolet light to said first sample to obtain a first reflection intensity Ic of said ultraviolet light reflected by said first sample;
   (c) applying said ultraviolet light to said second sample to obtain a second reflection intensity Ia of said ultraviolet light reflected by said pure amorphous silicon;
   (d) applying said ultraviolet light to said objective silicon film that is being evaluated to obtain a third reflection intensity Is of said ultraviolet light reflected by said objective silicon film;
   (e) comparing said first and second reflection intensities Ic and Ia with each other to obtain a first index value $\Delta Ka$;
   (f) comparing said first and third reflection intensities Ic and Is with each other to obtain a second index value $\Delta Ka$; and
   (g) comparing said first and second index values $\Delta Ka$ and $\Delta Ks$ with each other to evaluate said crystal rate in said objective silicon film.

2. The method of claim 1, wherein
said ultraviolet light has a plurality of components having different wavelengths in a predetermined wavelength region.

3. The method of claim 2, wherein
said step (e) comprises the steps of:
   (e-1) normalizing said second reflection intensity Ia by said first reflection intensity Ic to obtain a first normalized intensity Ka for said plurality of components; and
   (e-2) obtaining said first index value $\Delta Ka$ as a function of said first normalized intensity Ka; and
said step (f) comprises the steps of:
   (f-1) normalizing said third reflection intensity Is by said first reflection intensity Ic to obtain a second normalized intensity Ks for said plurality of components; and
   (f-2) obtaining said second index value $\Delta Ks$ as a function of said second normalized intensity Ks.

4. The method of claim 3, wherein
said step (e-2) comprises the steps of:
   (e-2-1) extracting a first minimum value Kra from respective values of said first normalized intensity Ka for said plurality of components;
   (e-2-2) obtaining first and second values of said first normalized intensity Ka corresponding to respective ends of said wavelength region;
   (e-2-3) interpolating said first and second values of said first normalized intensity to obtain a first interpolated value Kia; and
   (e-2-4) comparing said first minimum value Kra with said first interpolated value Kia to obtain said first index value $\Delta Ka$.

5. The method of claim 4, wherein
said step (f-2) comprises the steps of:
   (f-2-1) extracting a second minimum value Kra from respective values of said second normalized intensity Ks for said plurality of components;
   (f-2-2) obtaining first and second values of said second normalized intensity Ks corresponding to said respective ends of said wavelength region;
   (f-2-3) interpolating said first and second values of said second normalized intensity to obtain a second interpolated value Kis; and
   (f-2-4) comparing said second minimum value Krs with said second interpolated value Kis to obtain said second index value $\Delta Ks$.

6. The method of claim 5, wherein
said step (e-2-4) comprises the step of:
obtaining a first difference between said first minimum value Kra and said first interpolated value Kia to obtain said first index value $\Delta Ka$; and
said step (f-2-4) comprises the step of:
obtaining a second difference between said second minimum value Krs and said second interpolated value Kis to obtain said second index value $\Delta Ks$.

7. The method of claim 6, wherein
said step (e-2-4) comprises the step of:
obtaining a first difference between said first minimum value Kra and said first interpolated value Kia to obtain said first index value $\Delta Ka$; and
said step (f-2-4) comprises the step of:
obtaining a second difference between said second minimum value Krs and said second interpolated value Kis to obtain said second index value $\Delta Ks$.

8. The method of claim 7, wherein
said step (g) comprises the step of:
   (g-1) obtaining a ratio of said first and second index values $\Delta Ka$ and $\Delta Ks$; and
   (g-2) evaluating said crystal rate as a function of said ratio.

9. The method of claim 3, wherein
said step (e-2) comprises the steps of:
   (e-2-5) obtaining a first curve on a coordinate plane representing dependence of said first normalized intensity Ka on said plurality of components;
   (e-2-6) determining first and second points on said first curve corresponding to respective ends on said wavelength region;
   (e-2-7) determining a first line connecting said first and second points of said first curve;
   (e-2-8) determining a first area defined by said first line and said first curve; and
   (e-2-9) determining said first index value as a function of said first area.

10. The method of claim 9, wherein
said step (f-2) comprises the steps of:
   (f-2-5) obtaining a second curve on a coordinate plane representing dependence of said second normalized intensity Ks on said plurality of components;
   (f-2-6) determining first and second points on said second curve corresponding to said respective ends on said wavelength region;

(f-2-7) determining a second line connecting said first and second points of said second curve;

(f-2-8) determining a second area defined by said second line and said second curve; and (f-2-9) determining said second index value as a function of said second area.

11. The method of claim 1, wherein the step (a) comprises the step of:

(a-1) preparing one single-crystal silicon;

the step (b) comprises the step of:

(b-1) applying said ultraviolet light to said one single-crystal silicon to obtain a first value Ic1 of said first reflection intensity Ic;

(b-2) applying said ultraviolet light again to said one single-crystal silicon to obtain a second value Ic2 of said first reflection intensity Ic;

the step (c) comprises the step of:

(c-1) prior to the step (b-2), applying said ultraviolet light to said pure amorphous silicon to obtain said second reflection intensity Ia;

the step (d) comprises the step of:

(d-1) after the step (c-1), applying said ultraviolet light to said objective silicon film to obtain said third reflection intensity Is;

the step (e) comprises the step of:

comparing said first value Ic1 of said first reflection intensity Ic and said second reflection intensities Ia with each other to obtain said first index value $\Delta Ka$; and the step (f) comprises the step of:

comparing said second value Ic2 of said first reflection intensity Ic and said third reflection intensities Is with each other to obtain said second index value $\Delta Ks$.

* * * * *